United States Patent
Peritt et al.

(10) Patent No.: US 11,124,767 B2
(45) Date of Patent: Sep. 21, 2021

(54) USE OF APOPTOTIC CELLS EX VIVO TO GENERATE REGULATORY T CELLS

(71) Applicant: Mallinckrodt Pharmaceuticals Ireland Limited, Dublin (IE)

(72) Inventors: David Peritt, Bala Cynwyd, PA (US); Kim Campbell, Downingtown, PA (US); Amy Krutsick, Chester Springs, PA (US)

(73) Assignee: Mallinckrodt Pharmaceuticals Ireland Limited, Dublin (IE)

( * ) Notice: Subject to any disclaimer, the term of this patent is extended or adjusted under 35 U.S.C. 154(b) by 0 days.

(21) Appl. No.: 16/165,679

(22) Filed: Oct. 19, 2018

(65) Prior Publication Data

US 2019/0055516 A1 Feb. 21, 2019

Related U.S. Application Data

(60) Continuation of application No. 14/863,274, filed on Sep. 23, 2015, now Pat. No. 10,138,464, which is a division of application No. 11/579,319, filed as application No. PCT/US2006/042581 on Nov. 2, 2006, now Pat. No. 9,169,461.

(60) Provisional application No. 60/732,847, filed on Nov. 2, 2005.

(51) Int. Cl.
  *C12N 5/0783* (2010.01)
  *A61K 31/366* (2006.01)
  *A61K 31/59* (2006.01)
  *A61K 35/17* (2015.01)

(52) U.S. Cl.
  CPC .......... *C12N 5/0637* (2013.01); *A61K 31/366* (2013.01); *A61K 31/59* (2013.01); *A61K 35/17* (2013.01); *C12N 5/0636* (2013.01); *C12N 2500/38* (2013.01); *C12N 2501/15* (2013.01); *C12N 2501/23* (2013.01); *C12N 2501/231* (2013.01); *C12N 2501/39* (2013.01); *C12N 2502/11* (2013.01)

(58) Field of Classification Search
  CPC .......... C12N 5/0637; A61P 37/00; A61P 1/00
  See application file for complete search history.

(56) References Cited

U.S. PATENT DOCUMENTS

9,169,461 B2 * 10/2015 Peritt ............. A61K 31/59
2003/0133914 A1 * 7/2003 Edelson ......... A61K 49/0004
  424/93.7

OTHER PUBLICATIONS

Thornton et al. CD4+CD25+ Immunoregulatory T cells Suppress Polyclonal T cell Activation in vitro by inhibiting interleukin 2 production. The Journal of Experimental Medicine • vol. 188, No. 2, Jul. 20, 1998 287-296 (Year: 1998).*
Wang et al.Tumor-Specific Human CD4+ Regulatory T Cells and Their Ligands: Implications for Immunotherapy Immunity, vol. 20, 107-118, Jan. 2004, Copyright 2004 by Cell Press (Year: 2004).*
Boral et al.Disseminated Intravascular Coagulation Am J Clin Pathol 2016;146:670-680 (Year: 2016).*
Mackenzie et al. Creutzfeldt-Jakob disease:recent developments. F1000Research 2017, 6(F1000 Faculty Rev):2053 (Year: 2017).*
Schwartz et al.Breaking immune tolerance by targeting Foxp3 regulatory T cells mitigates Alzheimer's disease pathology.Nature Communications | 6:7967 | DOI: 10.1038/ncomms8967. 2015 (Year: 2015).*
Ciccocioppo et al.The Characterization of Regulatory T-Cell Profiles in Alzheimer's Disease and Multiple Sclerosis. Scientific Reports | (2019) 9:8788 | https://doi.org/10.1038/s41598-019-45433-3. (Year: 2019).*

* cited by examiner

*Primary Examiner* — Amy E Juedes
*Assistant Examiner* — Brian Hartnett (57) ABSTRACT

Many cell types in the body can remove apoptotic and cellular debris from tissues; however, the professional phagocyte, or antigen presenting cell ("APC"), has a high capacity to do so. The recognition of apoptotic cells ("ACs") occurs via a series of evolutionarily-conserved, AC associated molecular-pattern receptors ("ACAMPRs") on APCs that recognize and bind corresponding apoptotic-cell-associated molecular patterns ("ACAMPs"). These receptors recognize ligands such as phosphotidyl serine and oxidized lipids found on apoptotic cells. Savill et al. (2002); and Gregory et al. (2004).

8 Claims, 3 Drawing Sheets

USE OF APOPTOTIC CELLS EX VIVO TO GENERATE REGULATORY T CELLS

CROSS REFERENCE TO RELATED APPLICATIONS

This application is a continuation of pending U.S. application Ser. No. 14/863,274, filed Sep. 23, 2015, which is a division of U.S. application Ser. No. 11/579,319, filed Jul. 14, 2008, now U.S. Pat. No. 9,169,461, which claims the priority of PCT Application PCT/US2006/042581, filed Nov. 2, 2006 which claims the benefit of U.S. Provisional Patent Application No. 60/732,847, filed Nov. 2, 2005, each of which is hereby incorporated by reference in its entirety.

BACKGROUND OF THE INVENTION

Many cell types in the body can remove apoptotic and cellular debris from tissues; however, the professional phagocyte, or antigen presenting-cell ("APC"), has a high capacity to do so. The recognition of apoptotic-cells ("ACs") occurs via a series of evolutionarily-conserved, AC-associated molecular-pattern receptors ("ACAMPRs") on APCs that recognize and bind corresponding apoptotic-cell-associated molecular patterns ("ACAMPs"). These receptors recognize ligands such as phosphotidyl serine andoxidized lipids found on apoptotic cells. Saviii et al. (2002); and Gregory et al. (2004).

Both in vitro and in vivo that AC clearance by APCs in vivo regulates immune responses. Saviii, et al. (2002). This immune modulation appears to occur primarily via an alteration of APC function with several hallmarks of a tolerance-inducing APC. These tolerogenic APCs induce tolerance via a variety of mechanisms including the generation of regulatory T cells ("Tregs").

Tregs comprise a heterogeneous group of T lymphocytes, which actively inhibit immune responses. Groux et al. (1997); Sakaguchi et al. (2001); and Roncarolo et al. (2001). There is the potential to develop Treg therapies for a variety of diseases.

One way to generate Tregs in vivo is via the infusion of ACs. There is evidence from both animal models and human treatments that AC infusion, such as happens during extracorporeal photophoresis ("ECP"), induces Tregs. Maeda et al. (2005); Lamioni et al. (2005); Aubin et al. (2004); Mahnke et al. (2003); and Saas et al. (2002).

Other methods to generate Tregs ex vivo include exposing T cells to a variety of substances including: IL-10 (Roncarolo et al. (2001); and Zeller et al. (1999)); TGF.beta. (Zheng et al. (2004); Gray et al. (1998); Horwitz et al. (1999); Ohtsuka et al. (1999a); Ohtsuka et al. (1999b); Stohl et al. (1999); Gray et al. (2001); Horwiti (2001); Yamagiwa et al. (2001); Horwitz et al. (2002); and Zheng et al. (2002)); .alpha.MSH (Luger et al. (1999); Taylor (2005); Namba et al. (2002); Nishida et al. (1999); Nishida et al. (2004); Streilin et al. (2000); Taylor et al. (1992); Taylor et al. (1994a); Taylor et al. (1994b); Taylor et al. (1996); Taylor (1999); Taylor (2003); and Taylor et al. (2003)); vitamin D3 (Willheim et al. (1999); Penna et al. (2000); Pedersen et al. (2004); May et al. (2004); Koren et al. (1989); Gregori et al. (2001); Cobbold et al. (2003); and Barrat et al. (2002)); dexamethasone (Pedersen et al. (2004); Barrat et al. (2002); and O'Garra et al. (2003)); and purification (Earle et al. (2005); Schwarz et al. (2000); Chatenoud et al. (2001); Tang et al. (2004); and Masteller et al. (2005)).

Autoimmune diseases involve inappropriate activation of immune cells that are reactive against self tissue. These activated immune cells promote the production of cytokines and autoantibodies involved in the pathology of the diseases. Other diseases involving T-cells include Graft versus Host Disease (GVHD) which occurs in the context of transplantation. In GVHD donor T-cells reject recipient's tissues and organs by mounting an attack against the recipient's body. A host of other diseases involve disregulation of the host immune system. Some are best treated with pharmaceuticals, some with biologicals, others with treatments such as extracorporeal photophoresis (ECP), and yet others have very limited treatment options.

ECP has been shown to be an effective therapy in certain T cell-mediated diseases. In the case of GVHD, photophoresis has been used as a treatment in association with topical triamcinolone ointment, antifungal, antiviral, antibiotics, immunoglobulins, and methotrexate. ECP has also been used with immunosuppressive agents such as mycophenolate mofetil, tacrolimus, prednisone, cyclosporine, hydroxychloroquine, steroids, FK-506, and thalidomide for chronic GVHD ("cGVHD") and refractory cGVHD. For solid organ transplants, ECP has been used in conjunction with immunosuppressive agents to reduce the number of acute allograft rejection episodes associated with renal allografts and cardiac transplants. For example, ECP has been used with OKT3 and/or the immunosuppressive agents prednisone, azathioprine, and cyclosporine to reverse acute renal allograft rejection. ECP has also been used with cyclophosphamide, fractionated total body irradiation, and etoposide for allogeneic marrow transplantation for acute myeloid leukemia; acute lymphoblastic leukemia, chronic myeloid leukemia, non-Hodgkin's lymphoma; or severe aplastic anemia.

SUMMARY OF THE INVENTION

Ex vivo incubation with leukocytes in an allogeneic system leads to generation of T cells with regulatory activity. This generates regulatory T cells ("Treg cells" or "T regs") with activity to suppress immune responses against the alloantigen.

In an antigen specific and polyclonal activation systems an antigen specific result can be obtained by adding antigen or other stimulation with autologous apoptotic cells ("ACs").

The present invention encompasses a method of generating T cells with regulatory activity (T regs) by incubating leukocytes with autologous apoptotic peripheral blood mononuclear cells (ACs).

The present invention encompasses compositions of a population of T cells with regulatory activity (T regs) obtained by incubating leukocytes with autologous apoptotic peripheral blood mononuclear cells (ACs).

The present invention encompasses a method of treating autoimmune disorder or ameliorating one or more symptoms thereof, by administering to a patient in need thereof an effective amount of a composition of a population of T cells with regulatory activity (T regs) obtained by incubating autologous leukocytes with autologous apoptotic peripheral blood mononuclear cells (ACs).

The present invention encompasses a method of treating atopic disease or ameliorating one or more symptoms thereof by administering to a patient in need thereof an effective amount of a composition of a population of T cells with regulatory activity (T regs) obtained by incubating autologous leukocytes with autologous apoptotic peripheral blood mononuclear cells (ACs).

The present invention encompasses a method of administering to a transplant recipient an effective amount of a composition of a population of T cells with regulatory activity (T regs) obtained by incubating autologous leukocytes with autologous apoptotic peripheral blood mononuclear cells (ACs).

The present invention encompasses a method of administering to a GVHD patient an effective amount of a composition of a population of T cells with regulatory activity (T regs) obtained by incubating autologous leukocytes with autologous apoptotic peripheral blood mononuclear cells (ACs).

The present invention encompasses a method of treating patient with a disorder or the predisposition for a disorder by testing the patient to determine whether the patient has a disorder, and administering to a patient in need thereof an effective amount of a composition of a population of T cells with regulatory activity (T regs) obtained, by incubating autologous leukocytes with autologous apoptotic peripheral blood mononuclear cells (ACs).

DETAILED DESCRIPTION

Ex Vivo Generation of Tregs Using ACs

The systems that occur in vivo to generate Tregs are quite complex and rely on a series of cell types and morphologic location. Nevertheless, the present invention shows that it is possible to generate these cells in vitro under the conditions described herein. Ex vivo incubation with leukocytes in an allogeneic system leads to generation of T cells with regulatory activity. This generates regulatory T cells ("Treg cells") with activity to suppress immune responses against the alloantigen, important in a wide variety of disorders including, without limitation, autoimmune diseases, graft versus host disease ("GVHD.") and solid organ transplantation. In an antigen specific and polyclonal activation systems an antigen specific result can be obtained by adding antigen or other stimulation with autologous apoptotic cells ("ACs").

This ex vivo production method offers several advantages over the drug-induced methods previously described. Importantly, the possible toxic and non-natural effects of these added molecules are avoided.

In addition, there are advantages to ex vivo generation over the in vivo utilization of apoptotic cells including, without limitation, increased control over the number, activity and function of these cells. This therapeutic control provides improved patient treatment protocols.

Generating T regs using a series of methods such as purification, activation, and addition of differentiation factors such as TGF.beta., .alpha.MSH, anti-CD46, IL-10, vitamin D.sub.3 and dexamethasone has proven that these cells can be generated ex vivo. Apoptotic cells provide a more "in vitro-like" method to induce these cells by generating tolerogenic APCs.

The present invention encompasses a method of generating T cells with regulatory activity (T regs) by incubating leukocytes with autologous apoptotic peripheral blood mononuclear cells (ACs).

The present invention encompasses compositions of a population of T cells with regulatory activity (T regs) obtained by incubating leukocytes with autologous apoptotic peripheral blood mononuclear cells (ACs).

The present invention encompasses a method of treating autoimmune disorder or ameliorating one or more symptoms thereof, by administering to a patient in need thereof an effective amount of a composition of a population of T cells with regulatory activity (T regs) obtained by incubating autologous leukocytes with autologous apoptotic peripheral blood mononuclear cells (ACs).

Autoimmune disorders include, without limitation, acute transverse myelitis, alopecia areata, Alzheimer's disease, amyotrophic lateral sclerosis, ankylosing spondylitis, antiphospholipid syndrome, atherosclerosis, autoimmune Addison's disease, autoimmune hemolytic anemias Behcet's disease, bullous pemphigoid, cardiomyopathy, celiac sprue-dermatitis, Cerebellar Spinocerebellar Disorders, spinocerebellar degenerations (spinal ataxia, Friedreich's ataxia, cerebellar cortical degenerations), Chronic alcoholism, alcohol-induced hepatitis, autoimmune hepatitis, chronic fatigue immune dysfunction syndrome (CFIDS), chronic inflammatory bowel disease, chronic inflammatory demyelinating polyneuropathy, Churg-Strauss syndrome, cicatricial pemphigoid, cold agglutinin disease, CResT syndrome, Creutzfeldt-Jakob disease, Crohn's disease, Dejerine-Thomas atrophy, Dementia pugilistica, diabetes mellitus, Diffuse Lewy body disease, discoid lupus, disorders of the basal ganglia, disseminated intravascular coagulation, Down's Syndrome in middle age, drug-induced movement disorders, essential mixed cryoglobulinemia, fibromyalgia-fibromyositis, graft versus host disease, Graves' disease, Guillain-Barr syndrome, Hallerrorden-Spatz disease, Hashimoto's thyroiditis, Huntington's Chorea senile chorea, idiopathic pulmonary fibrosis, idiopathic thrombocytopenia purpura (ITP), IgA nephropathy, infantile or juvenile spinal muscular atrophy, insulin dependent diabetes, juvenile arthritis, KawaSaki's pathology, lesions of the corticospinal system, Leukemias, Hodgkin's lymphoma, non-Hodgkin's lymphoma, lichen planus, Meniere's disease, mixed connective tissue disease, multiple sclerosis, multiple systems degenerations (Mencet, Dejerine-Thomas, Shy-Drager, Machado-Joseph), myasthenia gravis; neurogenic muscular, Parkinson's disease, pemphigus vulgaris, pernicious anemia, polyarteritis nodosa, polychondritis, polyglandular syndromes, polymyalgia rheumatica, polymyositis dermatomyositis, primary agammaglobulinemia, primary biliary cirrhosis, Progressive supranuclear palsy, psoriasis, Raynaud's phenomenon, Reiter's syndrome, rheumatic fever, rheumatoid arthritis, sarcoidosis, scleroderma; Senile Dementia of Lewy body type, Sjogren's syndrome, stiff-Man syndrome, Subacute sclerosing panencephalitis, systemic disorders (Refsum's disease, abetalipoprotemia, ataxia, telangiectasia, mitochondrial multi-system disorder), systemic lupus erythematosus (SLE), Takayasu arteritis, temporal arteritis/giant cell arteritis, thyroidosis, ulcerative colitis, uveitis, vasculitis, vitiligo, Wegener's granulomatosis, Wernicke-Korsakoff syndrome.

The present invention encompasses a method of treating atopic disease or ameliorating one or more symptoms thereof by administering to a patient in need thereof an effective amount of a composition of a population of T cells with regulatory activity (T regs) obtained by incubating autologous leukocytes with autologous apoptotic peripheral blood mononuclear cells (ACs).

Atopic disorders include, without limitation, chronic inflammatory pathologies, and vascular inflammatory pathologies, including chronic inflammatory pathologies such as sarcoidosis, chronic inflammatory bowel disease, ulcerative colitis, and Crohn's pathology and vascular inflammatory pathologies, such as, but not limited to, disseminated intravascular coagulation, atherosclerosis, and Kawasaki's pathology, The present invention, encompasses a method of administering to a transplant recipient an effective amount of a composition of a population of T cells with regulatory activity (T regs) obtained by incubating autologous leukocytes with autologous apoptotic peripheral blood mononuclear cells (ACs).

The present invention encompasses a method of administering to a GVHD patient an effective amount of a composition of a population of T cells with regulatory activity (T regs) obtained by incubating autologous leukocytes with autologous apoptotic peripheral blood mononuclear cells (ACs).

The present invention encompasses a method of treating patient with a disorder or the predisposition for a disorder by testing the patient to determine whether the patient has a disorder, and administering to a patient in need thereof an effective amount of a composition of a population of T cells with regulatory activity (T regs) obtained by incubating autologous leukocytes with autologous apoptotic peripheral blood mononuclear cells (ACs).

T regs can be administered to the patient according to a schedule including, without limitation, two days, one week prior to the transplantation; three days, one week prior to harvesting said transplant; two days a week for two weeks prior to the transplantation; and three days a week for three weeks prior to the transplantation.

Effective amounts of T regs for use in the methods of treatment of the present invention to obtain the required clinical benefit in a subject may vary depending on the Source of cells, the subject's condition, the age and weight of the subject and other relevant factors, which are readily determinable by well-known methods. Preferably, the number of T regs administered to a patient are about $1 \times 10^5$/kg to about $1 \times 10^7$/kg. More preferably, the number of T regs administered to a patient are about $1 \times 10^6$/kg.

The method of the present invention encompasses incubating the ACs and leukocytes for a time and under conditions sufficient to generate T regs; Incubation can be under any condition known in the art to be suitable for leukocytes and for about 1 to about 14 days. Preferably, incubation is for about 8 days.

The method of the present invention can further include selecting leukocytes expressing CD4 to obtain CD4+ cells. Preferably, the cells are CD4+.

The method of the present invention includes incubation at any suitable concentration of ACs and CD4+ cells. Preferably, the cells are at about a 1:10 to about a 10:1 ratio of CD4+:ACs. More preferably, the cells are at a 2:1 to about a 1:2 ratio of CD4+:ACs.

The ACs of the present invention are obtained by an apoptosis-inducing treatment known in the art. Preferably, the apoptosis-inducing treatment is an ECP procedure that employs a photoactivatable compound together with light of a wavelength that activates the photoactivable compound. Preferably, the photoactivable compound is a psoralen and the light is UVA. Preferably, the psoralen is 8-MOP.

The method of the present invention can include the incubation with added factors that further enhance generation or function of the T regs. Suitable factors include, without limitation, are hormones, proteins, drugs or antibodies. Preferably, the factors include, without limitation, one of TGF.beta., .alpha.MSH, anti-CD46, IL-10, vitamin D.sub.3, dexamethasone, rapamycin and IL-2. Preferably, the factor is IL-10. Preferably, the IL-10 is present at a concentration of about 1 ng/ml to about 100 ng/ml. Preferably, the IL-10 is present at a concentration of about 20 ng/ml.

The method of the present invention includes adding an antigen to the incubation to generate Tregs which regulate immune response to the antigen. Preferably, the antigen is an alloantigen. Such antigens can be selected from any known in the art.

The cell populations useful in the methods of this invention comprise "apoptotic cells," which include cells and cell bodies, i.e., apoptotic bodies, that exhibit, or will exhibit, one or more apoptosis-characterizing features. An apoptotic cell may comprise any cell that is in the Induction phase, Effector phase, or the Degradation phase. The cell populations in the therapies of the invention may also comprise cells that have been treated with an apoptosis-inducing agent that are still viable. Such cells may exhibit apoptosis-characterizing features at some point, for example, after administration to the subject. Preferably, the ACs are autologous PBMCs that have been treated with an apoptosis inducer. Preferably the apoptosis inducer is ECP.

ECP directly induces significant levels of apoptosis. This has been observed, for example, in lymphocytes of CTCL, GVHD, and scleroderma patients. The apoptotic cells contribute to the observed clinical effect.

Apoptosis-characterizing features may include, but are not limited to, surface exposure of phosphatidylserine, as detected by standard, accepted methods of detection such as Annexin V staining; alterations in mitochondrial membrane permeability measured by standard, accepted methods evidence of DNA fragmentation such as the appearance of DNA laddering on agarose gel electrophoresis following extraction of DNA from the cells or by in situ labeling. Salvioli et al. (1997); Teiger et al. (1996); and Gavrieli et al. (1992).

The cell population for use in the present invention is induced to become apoptotic vivo, i.e., extracorporeally, and is compatible with those of the subject, donor, or recipient. A cell population may be prepared from substantially any type of mammalian cell including cultured cell lines. For example, a cell population may be prepared from a cell type derived from the mammalian subject's own body (autologous) or from an established cell line. Specifically, a cell population may be prepared from white blood cells of blood compatible with that of the mammalian subject, more'specifically, from the subject's own white blood cell and even more specifically, from the subject's own leukocytes or T cells.

A cell population may also be prepared from an established cell line. A cell line that may be useful in the methods of the present invention includes, for example, Jurkat cells (ATCC No. TIB-152). Other cells lines appropriate for use in accordance with the methods of the present invention may be identified and/or determined by those of ordinary skill in the art. The cell population may be prepared extracorporeally prior to administration, to the subject, donor, or recipient. Thus, in one embodiment, an aliquot of the subject's blood, recipient's blood, or the donor's blood may be withdrawn, e.g. by venipuncture, and at least a portion of the white cells thereof subjected extracorporeally to apoptosis-inducing conditions.

In one embodiment, the cell population may comprise a particular subset of cells including, but not limited to leukocytes or cells separated from leukocytes on the basis of their expression of CD4, that is CD4+ T cells. The separation and purification of blood components is well known to those of ordinary skill in the art. Indeed, the advent of blood component therapy has given rise to numerous systems designed for the collection of specific blood components. Several of these collection systems are commercially available from, for example, Immunicon Corp. (Huntingdon Valley, Pa.), Baxter International (Deerfield, Ill.), and Dynal Biotech (Oslo, Norway).

Immunicon's separation system separates blood components using magnetic nanoparticles (ferrofluids) coated with antibodies that conjugate, i.e., form a complex, to the target components in a blood sample. The blood sample is then incubated in a strong magnetic field and the target complex migrates away from the rest of the sample where it can then be collected. See, e.g., U.S. Pat. Nos. 6,365,362; 6,361,749; 6,228,624; 6,136,182; 6,120,856; 6,013,532; 6,013,188; 5,993,665; 5,985,153; 5,876,593; 5,795,470; 5,741,714; 5,698,271; 5,660,990; 5,646,001; 5,622,831; 5,597,531; 5,541,072; 5,512,332; 5,466,574; 5,200,084; 5,186,827; 5,108,933; and 4,795,698.

Dynal's Dynabeads® Biomagnetic separation system separates blood-components using magnetic beads coated with antibodies that conjugate to the target components in a blood sample, forming a Dynabeads-target complex. The complex is then removed from the sample using a Magnetic Particle Concentrator (Dynal MPC®). Several different cell types may be collected using this separation system. T cells and T cell subsets can also be positively or negatively isolated or depleted from whole blood, buffy coat, gradient mononuclear cells or tissue digests using, for example, CELLection™ CD2 Kit (Prod. No 116.03), Dynabeads® M-450 CD2 (Prod. No 111.01/02), Dynabeads® CD3 (Prod. No 111.13/14), Dynabeads® plus DETACHaBEAD (Prod. No. 113.03), Dynabeads® M-450 CD4 (Prod. No 111.05/06), CD4 Negative Isolation Kit (T helper/inducer cells) (Prod. No. 113.17), CD8 Positive Isolation Kit (Prod. No. 113.05), Dynabeads® CD8 (Prod. No. 111.07/08), CD8 Negative Isolation Kit (Prod. No. 113.19), T Cell Negative Isolation Kit. (Prod. No. 113.11), Dynabeads® CD25 (Prod. No 111.33/34), and Dynabeads® CD3/CD28 T Cell Expander (Prod. No. 111.31). Baxter International has developed several apheresis systems based on the properties of centrifugation, including the CS-3000 blood cell separator, the Amicus separator, and the Autopheresis-C system. The CS-3000 Plus blood cell separator collects both cellular apheresis, products and plasma. It comprises a continuous-flow separator with a dual-chamber centrifugal system that collects apheresis products. The Amicus operates in either a continuous-flow or intermittent-flow format to collect single donor platelets and plasma. The Autopheresis-C system is designed for the collection of plasma from donors and can collect more than 250 mL of plasma. See generally, U.S. Pat. Nos. 6,451,203; 6,442,397; 6,315,707; 6,284,142; 6,251,284; 6,033,561; 6,027,441; and 5,494,578.

In the most preferred embodiment of the invention, ECP is used to induce apoptosis. This involves a photoactivatable compound added to a cell population ex vivo. The photosensitive compound may be administered to a cell population comprising blood tells following its withdrawal from the subject, recipient, or donor, as the case may be, and prior to or contemporaneously with exposure to ultraviolet light. The photosensitive compound may be administered to a cell population comprising whole blood or a fraction thereof provided that the target blood cells or blood components receive the photosensitive compound. In another embodiment, a portion of the subject's blood, recipient's blood, or the donor's blood could first be processed using known methods to substantially remove the erythrocytes and the photoactive compound may then be administered to the resulting cell population comprising the enriched PBMC fraction.

Photoactivatable compounds for use in accordance with the present invention include, but are not limited to, compounds known as psoralens (or furocoumarins) as well as psoralen derivatives such as those described in, for example, U.S. Pat. Nos. 4,321,919; and 5,399,719. Preferred compounds include 8-methoxypsoralen; 4,5'8-trimethylpsoralen; 5-methoxypsoralen; 4-methyl psoralen; 4,4-dimethylpsoralen; 4-5'-dimethylpsoralen; 4'-aminomethyl-4,5',8-trimethylpsoralen; 4'-hydroxymethyl-4,5',8-trimethylpsoralen; 4',8-methoxypsoralen; and a 4'-(omega-amino-2-oxa) alkyl-4,5'8-trimethylpsoralen, including but not limited to 4'-(4-amino-2-oxa)butyl-4,5',8-trimethylpsoralen. In one embodiment, the photosensitive compound that may be used comprises the psoralen derivative, amotosalen (S-59) (Cerus Corp., Concord, Calif.). In another embodiment, the photosensitive compound comprises 8-methoxypsoralen (8 MOP).

The cell population to which the photoactivatable compound has been added is treated with a light of a wavelength that activates the photoactivatable compound. The treatment step that activates the photoactivatable compound is preferably carried out using long wavelength ultraviolet light (UVA), for example, at a wavelength within the range of 320 to 400 nm. The exposure to ultraviolet light during the photopheresis treatment preferably is administered for a sufficient length of time to deliver about 1-2 J/cm.sup.2 to the cell population.

Extracorporeal photopheresis apparatus useful in the methods according to the invention include those manufactured by Therakos, Inc., (Exton, Pa.) under the name UVAR®. A description of such an apparatus is found in U.S. Pat. No. 4,683,889. The UVAR® system uses a treatment system and consists of three phases including: 1) the collection of a buffy-coat fraction (leukocyte-enriched), 2) irradiation of the collected buffy coat fraction; and 3) reinfusion of the treated white blood cells. The collection phase has six cycles of blood withdrawal, centrifugation, and reinfusion steps. During each cycle, whole blood is centrifuged and separated in a pheresis bowl. From this separation, plasma (volume in each cycle is determined by the UVAR® instrument operator) and 40 ml buffy coat are saved in each collection cycle. The red cells and all additional plasma are reinfused to the patient before beginning the next collection cycle. Finally, a total of 240 ml of buffy coat and 300 ml of plasma are separated and saved for UVA irradiation.

The irradiation of the leukocyte-enriched blood within the irradiation circuit begins during the buffy coat-Collection of the first collection cycle. The collected plasma and buffy coat are mixed with 200 ml of heparinized normal saline and 200 mg of UVADEX® (water soluble 8-methoxypsoralin). This mixture flows in a 1.4 mm thick layer through the PHOTOCEPTOR® Photoactivation-Chamber, which is inserted between two banks of UVA lamps of the PHOTOSETTE®. PHOTOSETTE® UVA lamps irradiate both sides of this UVA-transparent PHOTOCEPTOR® chamber, permitting a 180-minute exposure to ultraviolet A light, yielding an average exposure per lymphocyte of 1-2 J/cm.sup.2. The final buffy coat preparation contains an estimated 20% to 25% of the total PBMC component and has a hematocrit from 2.5% to 7%. Following the photoactivation period, the volume is reinfused to the patient over a 30 to 45 minute period. U.S. patent application Ser. No. 09/480,893 describes another system for use in ECP administration. U.S. Pat. Nos. 5,951,509; 5,985,914; 5,984,887, 4,464,166; 4,428,744; 4,398,906; 4,321,919; WO 97/36634; and WO 97/36581 also contain description of devices and methods useful in this regard.

Another system that may be useful in the methods of the present invention is described in U.S. patent application Ser. No. 09/556,832. That system includes an apparatus by which the net fluid volume collected or removed from a subject may be reduced during ECP. The effective amount of light energy that is delivered to a cell population may be determined using the methods and systems described in U.S. Pat. No. 6,219,584.

A variety of other methods for inducing apoptosis in a cell population are well-known and may be adopted for use in the present invention. One such treatment comprises subjecting a cell population to ionizing radiation (gamma-rays, x-rays, etc.) and/or non-ionizing electromagnetic radiation including ultraviolet light, heating, cooling, serum deprivation, growth factor deprivation, acidifying, diluting, alkalizing, ionic strength change, serum deprivation, irradiating, or a combination thereof. Alternatively, apoptosis may be induced by subjecting a cell population to ultrasound.

Yet another method of inducing apoptosis comprises the extracorporeal application of oxidative stress to a cell population. This may be achieved by treating the cell population, in suspension, with chemical oxidizing agents such as hydrogen peroxide; other peroxides and hydroperoxides, ozone, permanganates, periodates, and the like. Biologically acceptable oxidizing agents may be used to reduce potential problems associated with residues and Contaminations of the apoptosis-induced cell population so formed.

In preparing the apoptosis-induced cell population, care should be taken not to apply excessive levels of oxidative stress, radiation, drug treatment, etc., because otherwise there may be a significant risk of causing necrosis of at least some of the cells under treatment. Necrosis causes cell membrane rupture and the release of cellular contents often with biologically harmful results, particularly inflammatory events, so that the presence of necrotic cells and their components along with the cell population comprising apoptotic cells is best avoided. Appropriate levels of treatment of the cell population to induce apoptosis; and the type of treatment chosen to induce apoptosis are readily determinable by those skilled the art:

One process according to the present invention involves the culture of cells from the subject, or a compatible mammalian cell line. The cultured cells may then be treated extracorporeally to induce apoptosis and to create a cell population therein. The extracorporeal treatment may be selected from the group consisting of antibodies, chemotherapeutic agents, radiation, ECP, ultrasound, proteins, and oxidizing agents. The cells, suspended in the subject's plasma or another suitable suspension medium, such as saline or a balanced mammalian cell culture medium, may then be incubated as indicated below.

Methods for the detection and quantitation of apoptosis are useful for determining the presence and level of apoptosis in the preparation to be incubated with leukocytes or T cells in the present invention. In one embodiment, cells undergoing apoptosis may be identified by a characteristic 'laddering' of DNA seen on agarose gel electrophoresis, resulting from cleavage of DNA into a series of fragments. In another embodiment, the surface expression of phosphatidylserine on cells may be used to identify and/or quantify an apoptosis-induced cell population. Measurement of changes in mitochondrial membrane potential, reflecting changes in mitochondrial membrane permeability, is another recognized method of identification of a cell population. A number of other methods of identification of cells undergoing apoptosis and of a cell population, many using monoclonal antibodies against specific markers for a cell population, have also been described in the scientific literature.

The administration of T regs finds utility in treating arthritis and other autoimmune diseases. They are also useful in the treatment or prophylaxis of at least one autoimmune-related disease in a cell, tissue, organ, animal, or patient including, but not limited to, acute transverse myelitis, alopecia areata, Alzheimer's disease, amyotrophic lateral sclerosis, ankylosing spondylitis, antiphospholipid syndrome, atherosclerosis, autoimmune Addison's disease, autoimmune hemolytic anemia, Behcet's disease, bullous pemphigoid, cardiomyopathy, celiac sprue-dermatitis, Cerebellar Spinocerebellar Disorders, Spinocerebellar degenerations (spinal ataxia, Friedreich's ataxia; cerebellar cortical degenerations), chronic alcoholism, alcohol-induced hepatitis, autoimmune hepatitis, chronic fatigue immune dysfunction syndrome (CFIDS), chronic inflammatory bowel disease, chronic inflammatory demyelinating polyneuropathy, Churg-Strauss syndrome, cicatricial pemphigoid, cold agglutinin disease, CResT syndrome, Creutzfeldt-Jakob disease, Crohn's disease, Dejerine-Thomas, Dementia pugilistica, diabetes mellitus, Diffuse Lewy body disease, discoid lupus, disorders of the basal ganglia, disseminated intravascular coagulation, Down's Syndrome in middle age, drug-induced movement disorders, essential mixed oryoglobulinerhia; fibromyalgia-fibromyositis, graft versus host disease, Graves' disease, Guillain-Barr, Hallerrorden-Spatz disease, Hashirboto's thyroiditis, Huntington's Choreasenile chorea, idiopathic pulmonary fibrosis, idiopathic thrombocytopenia purpura (ITP), IgA nephropathy, infantile or juvenile spinal muscular atrophy, insulin dependent diabetes, juvenile arthritis, Kawasaki's pathology, lesions of the corticospinal system; Leukemias, Hodgkin's lymphoma, non-Hodgkin's lymphoma, lichen planus, Meniere's disease, mixed connective tissue disease, multiple sclerosis, multiple systems degenerations (Mencel, Dejerine-Thomas, Shy-Drager, Machado-Joseph), myasthenia gravis, neurogenic muscular, Parkinson's disease, pemphigus vulgaris, pernicious anemia, polyarteritis nodosa, polychondritis, polyglandular syndromes, polymyalgia rheumatica, polymyositis dermatomyositis, primary agammaglobulinemia, primary biliary cirrhosis, Progressive supranuclear palsy, psoriasis, Raynaud's phenomenon, Reiter's syndrome, rheumatic fever, rheumatoid arthritis, sarcoidosis, scleroderma, Senile Dementia of Lewy body type, Sjogren's syndrome, stiff-man syndrome, Subacute sclerosing panencephalitis, systemic disorders (Refsum's disease, abetalipdprotemia, ataxia, telangiedtasia, mitochondrial multi-system disorder), systemic lupus erythematoSus (SLE), Takayasu arteritis, temporal arteritis/giant cell arteritis, thyroidosis, ulcerative colitis, uveitis, vasculitis, vitiligo, Wegener's granulomatosis, Wernicke-Korsakoff syndrome.

The present invention is also useful in treating graft rejection or graft versus host disease (GVHD). Acute solid organ transplantation rejection occurs in 30% to 60% of patients after lung transplantation and to a lower degree with liver, kidney, heart etc. due to the success of immunosuppressive agents. The lymphocyte (cell)-mediated immune reaction against transplantation antigens is the principal mechanism of acute rejection. A delayed or chronic rejection causes graft destruction in months to years after transplantation and is characterized by vascular destruction leading to necrosis of the transplanted tissue. This rejection is not currently suppressed to any large degree by standard regimens and thus the need for more sustainable immune tolerance is a significant unmet need.

Late graft deterioration occurs occasionally, and this chronic type of rejection often progresses insidiously despite increased immunosuppressive therapy. The pathologic picture differs from that of acute rejection. The arterial endothelium is primarily involved, with extensive proliferation that may gradually occlude the vessel lumen, resulting in ischemia and fibrosis of the graft.

Immunosuppressants are currently widely used to control the rejection reaction and are primarily responsible for the success of transplantation. However, these drugs suppress all immunologic reactions, thus making overwhelming infection the leading cause of death in transplant recipients.

Existing immunosuppressant treatment can differ in the case of different types of transplants. Liver allografts are less aggressively rejected than other organ allografts. For example, hyperacute rejection of a liver transplant does not occur invariably in patients who were presensitized to HLA antigens or ABO incompatibilities. Typical immunosuppressive therapy in an adult involves using cyclosporine, usually given IV at 4 to 6 mg/kg/day starting at the time of transplantation and then 8 to 14 mg/kg/day po when feeding is tolerated. Doses are adjusted, downward if renal dysfunction occurs, and blood levels are used as approximate measures of adequate dosage.

In heart transplantation, immunosuppressive regimens are similar to those for kidney or liver transplantation. However, in lung and heart-lung transplants acute rejection occurs in >80% of patients but may be successfully managed. Patients are treated with corticosteroids, given rapidly IV in high dosage, ATG, or OKT3. Prophylactic ALG or OKT3 is also frequently given during the first two post-transplant weeks. Pancreas transplantation is unique among the vascularized organ transplants: instead of being used to save a life, it attempts to stabilize or prevent the devastating target organ complications of type I diabetes. Because the recipient exchanges the risks of insulin injection with the risks of immunosuppression, pancreas transplantation has been generally limited primarily to patients who already need to receive immunosuppressive drugs (i.e., diabetics with renal failure who are receiving a kidney transplant);

Patients with acute myeloid or lymphoblastic leukemia may benefit from bone marrow transplant (BMT). Pediatric BMT has expanded because of its potential for curing children with genetic diseaks (e.g., thalasseinia, sickle cell anemia, immunodeficiencies, inborn errors of metabolism). Another option for BMT is autologous transplantation (removal of a patient's own marrow when a complete remission has been induced, followed by ablative treatment of the patient with the hope of destruction of any residual tumor and rescue with the patient's own bone marrow). Since an autograft is used no immunosuppression is necessary other than the short-term high-dose chemotherapy used for tumor eradication and bone marrow ablation; post transplant problems with GVHD are minimal.

The rejection rate is <5% in transplants for leukemia patients from HLA-identical donors. For multiply transfused patients with aplastic anemia, the rejection rate has also been significantly decreased because of increased immunosuppression during transplant induction. Nonetheless, complications can arise including rejection by the host of the marrow graft; acute GVHD, and infections. Later complications include chronic GVHD, prolonged immunodeficiency, and disease recurrence.

Numerous other transplantations can be made more effective with the treatment of the present invention. Examples include, corneal transplantation, skin allografts, cartilage allografts, bone, grafts, and small bowel transplants.

A host of other disorders can be treated more effectively using the methods of the present invention. For example, cutaneous T cell lymphoma is a disease in which T lymphocytes become malignant and affect the skin. Three kinds of treatment are commonly used radiation; chemotherapy; and photopheresis. Treatment of cutaneous T cell lymphoma depends on the stage of the disease, and the patient's age and overall health. Standard treatment may be considered because of its effectiveness in patients in past studies, or participation in a clinical trial may be considered. Most patients with cutaneous T cell lymphoma are not cured with standard therapy and some standard treatments may have more side effects than are desired. Treatment using the method of the present invention cantle used in the treatment of this disease as well.

The methods of the present invention may also be used in implant surgery, for example, with implant surgery commonly performed in cosmetic or non-cosmetic plastic surgery. Such implants may include dental, fat grafting, for example to the cheeks, lips and buttocks, facial implants, including those to the nose, cheeks, forehead, chin and skull, buttocks implants, breast implants, etc. Other implants include, but are not limited to, corneal ring, cortical, orbital, cochlear, muscle (all muscles, including pectoral, gluteal, abdominal, gastrocnemius, soleus, bicep, tricep), alloplastic joint and bone replacement, bone repair implants (screws, rods, beams; bars, springs), metal plates, spinal, vertebral' hair, botox/collagen/restylane/perlane injections, penile implants, prostate seed implants, breast implants (cosmetic and reconstructive), intrauterine devices, hormonal implants; fetal or stem cell implantation, pacemaker, defibrillator, artificial arteries/veins/valves, and artificial organs.

Autoimmune diseases can also be more effectively treated using the methods of the present invention. These are diseases in which the immune system produces autoantibodies to an endogenous antigen, with consequent injury to tissues. Individuals may be identified as having a disease by several methods, including, but not limited to, HLA linkage typing, blood or serum-based assays, or identification of genetic variants, e.g., single nucleotide polymorphisms (SNPs). For example, once an individual is determined to have the HLA DR4 linkage and has been diagnosed to have rheumatoid arthritis, T reg treatment can be prescribed. Other HLA alleles, also known as MHC alleles, that are associated with autoimmune diseases include B27 (Ankylosing spondylitis); DQA1*0501 and DQB1*0201 (Celiac disease); DRB1*03, DRB1*04, DQB1*0201, DQB1*0302, and DMA*0101 (Type I Diabetes); and Cw6 (Psoriasis). These alleles may also be used to determine whether an individual is experiencing an autoimmune disease and, thus, whether T reg treatment may be efficacious.

Blood- or serum-based assays may be used to assess predisposition to a disease. There is, for example, an assay that detects the presence of autonuclear antibodies in serum, which may lead to the onset of lupus. Serum-based assays also exist for predicting autoimmune myocarditis. In addition, serum-based assays may be used to determine insulin levels (diabetes) or liver or heart enzymes for other diseases. T3 levels may be predictive of Hashimotos thyroiditis. After an individual is determined to be having a disease using a blood or serum-based assay, the methods of the present invention may be used to prevent, or delay the onset of, or reduce the effects of these diseases. Individuals may be identified as being predisposed for disease through the identification of genetic variations, including, but not limited to, SNPs. Thus, in a further aspect of the invention, a determination is first made that a patient has an autoimmune disorder or is predisposed to one and that patient is then prescribed treatment with T regs.

The methods of this invention are also applicable to the treatment of atopic diseases, which are allergic diseases in which individual are very sensitive to extrinsic allergens. Atopic diseases include, but are not limited to, atopic dermatitis, extrinsic bronchial asthma, urticaria, allergic rhinitis, allergic enterogastritis and the like. Standard diagnostic tests can be used to determine whether a patient has a disorder of the type described above.

The following examples are provided to illustrate but not limit the claimed invention. All references cited herein are hereby incorporated herein by reference.

Example 1

Apoptotic Induction Via 8MOP/UVA

Normal donor human leukocytes-were passed over Ficoll-paque and PBMC collected and washed before placing at approximately $10.^7$ cells/rill in a T-75 tissue culture flask. To this flask 200 ng/ml 8-MOP was added before UVA irradiation (.about.3 J/cm.$^2$). Cells were quickly removed from the flask, in order to avoid adherence, and placed at the appropriate concentration for Treg generation.

Treg Generation

Figure 1:
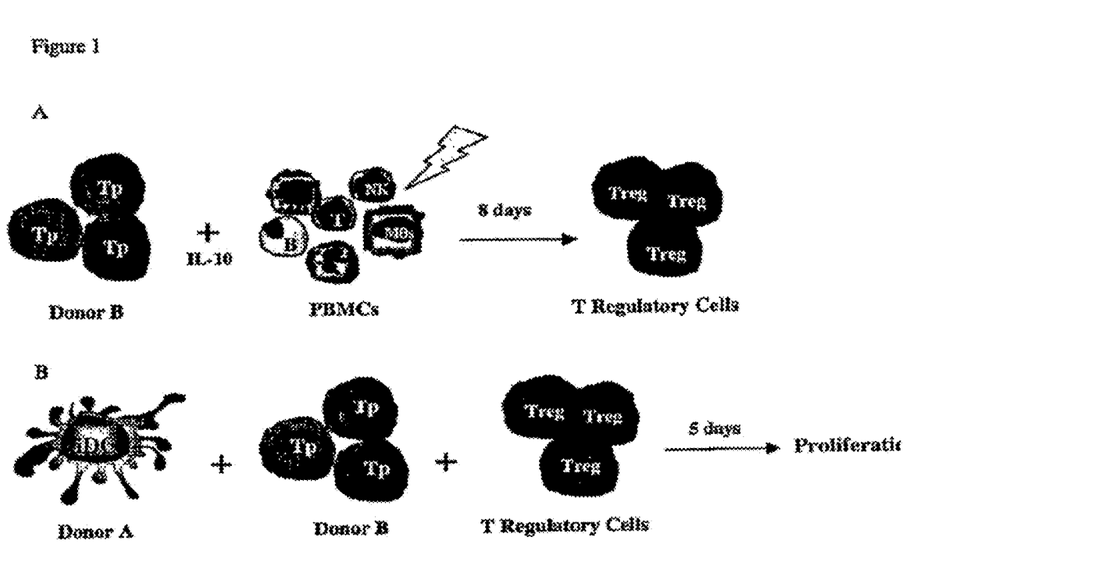
FIG. 1 is a schematic showing A: Treg Generation; B: After T regulatory cells are generated, Treg cells placed into MLR.

Normal donor human leukocytes were passed over Ficoll-paque and PBMC were collected. T lymphocytes were purified from PBMCs using magnetically activated cell sorter columns and $CD4^+$ negative selection antibody cocktail (Miltenyi Biotec). The purified nave CD4 T cells were co-incubated with ECP-treated PBMCs at a 2:1 ratio (CD4:PBMCs) with 20 ng/ml IL-10 for 8 days (FIG. 1A). After 8 days, the $CD4^+$ T cells were purified using MACs and CD4 positive selection antibody cocktail (Miltenyi Bioteh). IL-10 is not required but in some instances, induces a more consistent phenotype.

Treg Evaluation

Treg suppressive activity was evaluated by a secondary mixed lymphocyte reaction ("MLR") (FIG. 1B). Syngeneic $CD4.^+$ T cells were placed in a 96 well plate at 10,000, cells/well. Allogeneic dendritic cells were added to the well at 2000 cells per well. The Tregs were titrated into the MLR starting at a ratio of 1 Treg cell to 4 responder T cells. Proliferation was measured on day 5 by bromodeoxyuridine ("BRDU") incorporation using Roche's Cell Proliferation BRDU chemiluminescent ELISA. Chemiluminescence was measured using TopCount (Perkin Elmer):

Example 2

T Reg Activity is Found in Generation of T Cells by the Present Method

Figure 2:
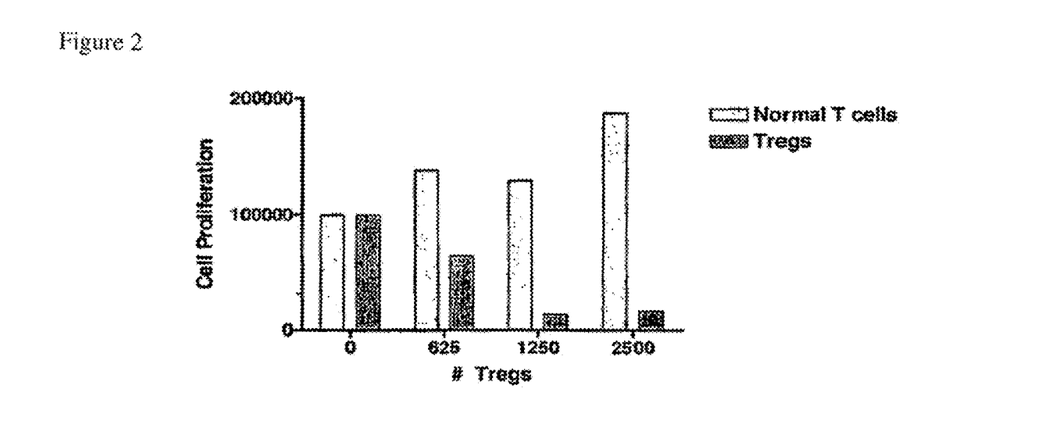
FIG. 2 shows that regulatory T Cells generated via Co-incubation with ECP-treated PBMCs inhibit the proliferation of syngeneic T Cells

CD4+ T cells were incubated with ECP treated peripheral blood cells for 8 days in the presence of 20 ng/mL IL-10. T regs were purified from the culture using MACs and CD4 positive selection antibody cocktail (Miltenyi Biotec). To assess their regulatory activity, the T regs were then added into an MLR consisting of 10,000 syngeneic CD4+ T cells and 2000 allogeneic dendritic cells. Proliferation in these cultures was measured on day 5 by BRDU incorporation. The results are shown in FIG. 2.

Example 3

T Reg Activity is Found in Generation of T Cells by the Present Method

Figure 3:
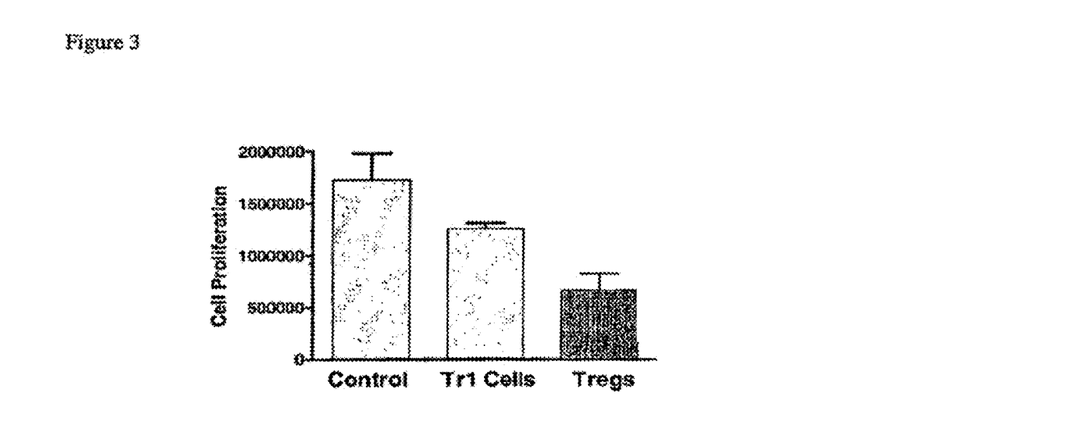
FIG. 3 shows that regulatory T Cells generated via co-incubation with ECP-treated PBMCs inhibit T Cell proliferation better than standard Tr1 cells.

Tr1 cells were generated by incubating CD4+T cells in the presence of 20 ng/ml IL-10. T regs were generated by incubating CD4+ T cells with ECP treated peripheral blood cells for 8 days in the presence of 20 ng/ml IL-10. T regs were purified from the culture using MACs and CD4 positive selection antibody cocktail (Miltenyi Biotec). To assess their regulatory activity, the T regs were then added into an MLR consisting of 10,000 syngeneic CD4+ T cells and 2000 allogeneic dendritic cells. Proliferation in these cultures was measured on day 5 by BRDU incorporation. The results are shown in FIG. 3.

Example 4

T Reg Phenotype is Found in Generation of T Cells with the Present Method

Figure 4:
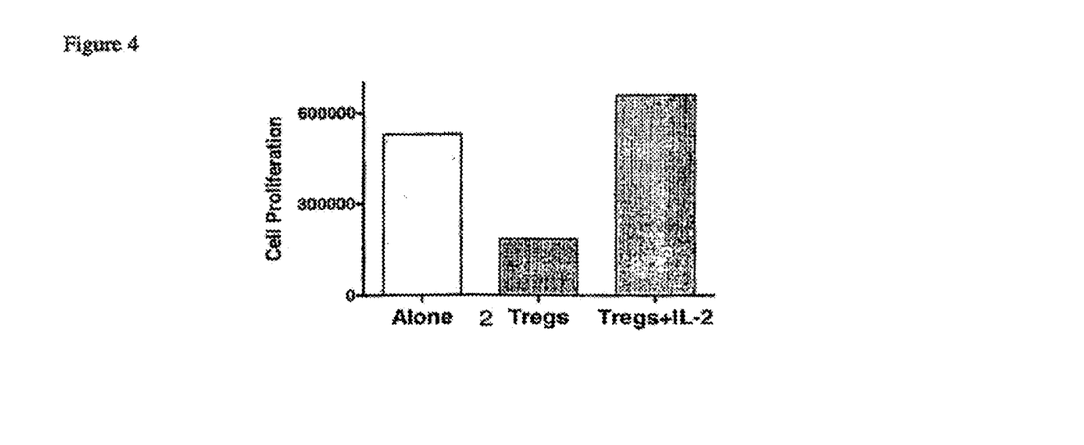
FIG. 4 shows that generation of Regulatory T Cells via co-incubation with ECP-treated PBMCs can be reversed through the addition of Interleukin-2.

CD4+ T cells were incubated with ECP treated peripheral blood cells for 8 days in the presence of 20 ng/mL IL-10. T regs were purified from the culture using MACS and CD4 positive selection antibody cocktail (Miltenyi Biotec). The T regs were then added to an MLR consisting of 10,000 syngeneic CD4+ T cells and 2000 allogeneic dendritic cells. IL-2 was added to the MLR at 2 ng/n11. Proliferation in these cultures was measured on day 5 by BRDU incorporation. The results are shown in FIG. 4.

Example 5

T Reg Phenotype is Found in Generation of T Cells with the Present Method

Figure 5:
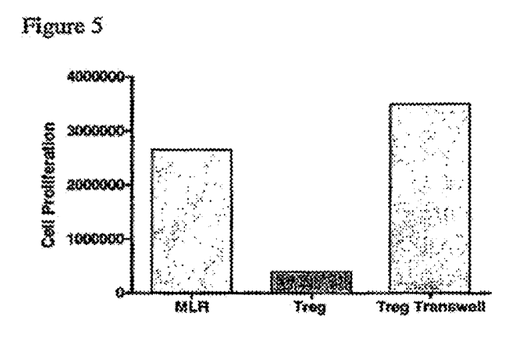
FIG. 5 shows that suppressive activity of regulatory T cells generated via co-incubation with ECP-treated PBMCs is contact-dependent.

Tregs generated by co-incubation with ECP-treated PBMCs were evaluated in a MLR using a 24-well transwell insert system (Nunc Tissue Culture 0.2 .mu.M Anopore Insert system #136935). A MLR consisting of 500,000 syngeneic CD4+ T cells and 100,000 allogeneic dendritic cells were-placed in the bottom portion of the transwell. 250,000 Tregs were placed in either the transwell insert or directly into the bottom well with the responder T cells and allogeneic dendritic cells. On day 5, the inserts were removed and proliferation was measured on day 5 by BRDU incorporation. The results shown in FIG. 5.

Example 6

(Mouse Model In Vivo Application) (Prophetic)

Mice

Male C3H/HeJ (C3H; H2k), (B6XC3H)F1 (H2bXk), (B6XDBA/2)F1 (H2bXd), C57BL/6 (B6; H2b), and CBA/JCr (CBA; H2k) mice will be purchased from the National Cancer Institute Research and Development Center (Frederick, Md.). B10.BR (H2k) mice will be purchased from the Jackson Laboratories (Bar Harbour, Me.). Mice used for experiments will be between 6-10 weeks of age, and housed in sterile microisolator cages within a specific pathogen-free facility, receiving autoclaved food and water ad libitum.

Media

Phosphate-buffered saline (PBS) supplemented with 0.1% bovine serum albumin (BSA; Sigma Chemical Co., St Louis, Mo.) will be used for all in vitro manipulations of the donor bone marrow and lymphocytes. Immediately-prior to injection, the cells will be washed and resuspended in PBS alone. For maintaining cell lines and for in vitro assays, RPMI 1640 medium (Mediatech, Herndon, Va.) will be used, supplemented with 10% fetal bovine serum (FBS; GIBCO, Grand Island, N.Y.), 2 mmol/L L-glutamine, 50 IU/mL penicillin, and 50 .mu.g/mL streptomycin.

Antibodies

Experimental Photopheresis

Splenocytes will be harvested from syngeneic littermate healthy mice and made into single cell suspension by grinding with the back end of a syringe in PBS. These cells will be resuspended and cells washed twice with PBS before re-suspending at 12.5.times.10.sup.6 cells/mL PBS. Upon washing cells they will be resuspended in ice-cold medium and seeded at approximately 106 cells/ml in a T75 flask. Psoralen (UVADEX solution) will be added to a final concentration of 200 ng/ml, which is a 100 fold dilution from the stock solution provided by Therakos. The flask will be placed lying down in the UVA irradiation chamber and given approximately 1.5 J/cm.sup.2 of light which corresponds to 1.5 minutes of bottom light when the tray is 6 cm from the light source. Cells will be quickly removed from the flask to avoid adherence and placed at the appropriate concentration for injection. If there is adherence, the flask will be gently scraped or tapped to remove most of the cells.

Bone Marrow Transplantation

Bone marrow will be harvested from the tibia and femurs of donor mice by flushing with PBS containing 0.01% BSA (PBS/BSA). Bone marrow cells will be depleted of T cells using an anti-Thy 1.2 nAb (J1j; American Type Culture Collection, Rockville, Md.) at a 1:100 dilution and guinea pig complement (Rockland Imrnunochemicals, Gilbertsville, Pa.) at a dilution of 1:6 for 45 minutes at 37.degree. C. Lymphocytes will be isolated from spleens and lymph nodes of donor mice. Splenocytes will be treated with Gey's balanced salt lysing solution containing 0.7% ammonium chloride (NH.sub.4Cl) to remove red blood cells (RBCs). After RBC depletion, spleen and lymph node cells will be pooled and depleted of B cells by panning on a plastic Petri dish, precoated with a 5 mg/ml dilution of goat anti-mouse IgG for 1 hour at 4.degree. C. These treatments are expected to result in donor populations of approximately 90%-95% CD3+ cells, as quantitated by fluorescent flow cytometry. T cells subsets will be then isolated via negative selection using either anti-CD8 (3.168) or anti-CD4 mAb (RL172) and complement. These, treatments are expected to reduce the targeted T cell, subset populations to background levels, as determined by flow cytometric analysis. Recipient mice will be exposed to 13 Gy whole body irradiation from a 137CS source at 1.43 Gy/min, delivered in a split dose of 6.5 Gy each, separated by 3 hours. These mice will be then be transplanted with 2.times.10.sup.6 anti-Thy 1.2 treated bone marrow cells (ATBM; T cell-depleted) along with the indicated, number of appropriate T ceM (donor CD4 or CD8 enriched T cells), intravenously (i.v.)' via the tail vein. Mice will be treated with T regs 1 day before transplantation and again on days 0, 4, 8, and 12 (all at 0.5 mg; i.p.). For GVL experiments, B6 recipient mice will be challenged with an injection of T regs one day before transplantation of donor ATBM and T cells, with a similar schedule of T reg treatment. In both GVHD and GVL experiments, the mice will be checked daily for morbidity and mortality until completion. The data will be pooled from 2-3 separate experiments, and median survival times (MST) will be determined as the interpolated 50% survival point of a linear regression through all of the day of death data points, including zero. Statistical comparisons for survival between experimental groups will be performed by the nonparametric Wilcoxon signed rank test. Significance for weight comparisons will be determined by the T-test at individual time points.

Flow Cytometry

Appropriate mAbs in volumes of 25 .mu.L will be incubated with 2-5.times.10.sup.5 cells in the wells of a 96-well U-bottom microplate at 4.degree. C. for 30 minutes, centrifuged at 1500 rpm for 3 minutes, and washed with PBS containing 0.1% BSA and 0.01% sodium azide (wash buffer). The percentage positive cells, and the arithmetic mean fluorescence intensity will be calculated for each sample.

Pathological Analysis

Full thickness ear biopsies (3.times.2 mm) will be sampled from each mouse of the various treatment groups and immediately fixed in 4% glutaraldehyde overnight and then rinsed with 0.1 M sodium cacodylate buffer (pH 7.4). Tissues will be post-fixed with 2% osmium tetroxide for 2 h, dehydrated in graded ethanol and embedded in Epon 812. One-micron-thick sections will be cut with a Porter-Blum MT2B ultramicrotome, stained with toluidine blue, and finally dipped in 95% ethanol for light microscopic analysis. The number of dyskeratotic epidermal cells/linear mm, as previously determined, will be counted under a .times.100 objective and a .times.10 eye piece of a light microscope. More than ten linear mm of the epidermis will be assessed in each animal and each time point. The analysis will be performed under blinded conditions as to the treatment groups.

Additional animal models for T regs are provided for instance by 20030157073; Kohm, A et al. (2002); Tang, Q et al. (2004); and Schwarz, A et al. (2004).

REFERENCES

Aubin et al. (2004) "Ultraviolet light-induced regulatory (suppressor) Tcells: an approach for promoting induction of operational allograft tOlerance?" Transplantation 77(1 Suppl):S29-31

Chatenoud et al. (2001) "Suppressor T cells—they're back and critical for regulation of autoimmunity" Immunol Rev 182:149-163

Cobbold et al. (2003) "Regulatory T cells and dendritic cells in transplantation tolerance: molecular markers and mechanisms" Immunol Rev 196:109-124

Earle et al. (2005) "In vitro expanded human CD4+CD25+ regulatory T cells suppress effector T cell proliferation" Clin Immunol 115:3-9

Gavrieli et al. (1992) Identification of programmed cell death in situ via specific labeling of nuclear DNA fragmentation J Cell Biol 119:493-501

Gray et al. (1998) "Generation of an inhibitory circuit involving CD8+ T cells, IL-2, and NK cell-derived TGF-beta: contrasting effects of anti-CD2 and anti-CD3" J Immunol 160:2248-2254.

Gray et al. (2001) "Transforming growth factor beta enhances the expression of CD154 (CD40L) and production of tumor necrosis factor alpha by human T lymphocytes" Immunol Lett 78:83-88

Gregori et al. (2001) "Regulatory T cells induced by 0.1 alpha,25-dihydroxyvitamin D3 and mycophenolate mofetil treatment mediate transplantation tolerance" J Immunol 167:1945-1953

Gregory et al. (2004) "The macrophage and the apoptotic cell: an innate immune interaction viewed simplistically?" Immunol 113:1-14

Groux et al. (1997) "A CD4+ T-cell subset inhibits antigen-specific T-cell responses and prevents colitis" Nature 389:737-742

Horwitz (2001) "Peripheral blood CD4+ T cells in systemic lupus erythematosus" Lupus 10:319-320

Horwitz et al. (1999) "Role of NK cells and TGF-beta in the regulation of T-cell-dependent antibody production in health and autoimmune disease" Microbes Infect 1:1305-1311

Horwitz et al. (2002) "The potential of human regulatory T tells generated ex vivo as a treatment for lupus and other chronic inflammatory diseases" Arthritis Res 4:241-246

Koren et al. (1989) "1,25-Dihydroxyvitamin D3 acts directly on human lymphocytes and interferes with the cellular response to interleukin-2" Immunopharmacology 18:187-194

Lamioni et al. (2005) "The immunological effects of extracorporeal photopheresis unraveled: induction of tolerogenic dendritic cells in vitro and regulatory T cells in vivo" Transplantation 79:846450

Luger et al. (1999) "Role of epidermal cell-derived alpha-melanocyte stimulating hormone in ultraviolet light mediated local immunosuppression" Ann NY Acad Sci 885: 209-216

Maeda et al. (2005) "Intravenous infusion of syngeneic apoptotic cells by photopheresis induces antigen-specific regulatory T cells" J Immunol 174:5968-5976

Mahnke et al. (2003) "Induction of CD4+/CD25+ regulatory T cells by targeting of antigens to immature dendritic cells" Blood 101:4862-2869

Masteller et al. (2005) "Expansion of Functional Endogenous Antigen-Specific CD4+CD25+ Regulatory T Cells from Nonobese Diabetic Mice" J Immunol 175:3053-3059

May et al. (2004) "Immunoregulation through 1,25-dihydroxyvitamin D3 and its analogs" Curr Drug Targets Inflamm Allergy 3:377-393

Narnba et al. (2002) "Induction of regulatory T cells by the immunomodulating cytokines alphaimelanocyte-stimulating hormone and transforming growth factor-beta2" J Leukoc Biol 72:946-952

Nishida et al. (1999) "Specific aqueous humor factors induce activation of regulatory T cells" Invest Ophthalmol. Vis Sci 410:2268-2274

Nishida et al. (2004) "Anti-inflammatory effects a alpha-melanocyte-stimulating hormone against rat endotoxin-induced uveitis and the time course of inflammatory agents in aqueous humor" Int Immunopharmacol 4:1059-1066

O'Garra et al. (2003) "In vitro generation of IL-10-producing regulatory CD4+ T cells is induced by immunosuppressive drugs and inhibited by Th1- and Th2-inducing cytokines" Immunol Lett 85:135-139

Ohtsuka et al. (1999a) "Cytokine-mediated down-regulation of B cell activity in SLE: effects of interleukin-2 and transforming growth factor-beta" Lupus 8:95-102

Ohtsuka et al. (1999b) "The relationship between defects in lymphocyte production of transforming growth factor-beta1 in systemic lupus erythematosus and disease activity or severity" Lupus 8:90-94

Pedersen et al. (2004) "Induction of regulatory dendritic cells by dexamethasone and 1 alpha,25-Dihydroxyvitarnin D(3)" Immunol Lett 91:63-69

Penna et al. (2000) "1 Alpha,25-dihydroxyvitamin D3 inhibits differentiation, Maturation, activation, and survival of dendritic cells leading to impaired alloreactive T cell activation" J Immunol 164:2405-2411

Roncarolo et al. (2001) "Type 0.1 T regulatory cells" Immunol Rev 182:68-79

Saas et al. (2002) "Cell-based therapy approaches using dying cells: from tumour immunotherapy to transplantation tolerance induction" Expert Opin Biol Ther 2:249-263.

Sakaguchi et al. (2001) "Immunologic tolerance maintained by CD25+CD4+ regulatory T cells: their common role in controlling autoimmunity, tumor immunity, and transplantation tolerance" Immunol Rev 182:1832

Salvioli et al. (1997) FEBS Let 411:77-82

Savill et al. (2002) "A blast from the past: clearance of apciptotic cells regulates immune responses" Nat Rev Imniunol 2:965-975

SchWatz et al. (2000) "Evidence for functional relevance of CTLA-4 in ultraViolet-radiation-indUced tolerance" J Immunol 165:1824-1831

Stohl et al. (1999) "Impaired cytotoxic T lymphocyte activity in systemic lupus erythematosus following in vitro polyclonal T cell stimulation: a contributory role for non-T cells" Luput 8:293-299

Streilein et al. "Neural control of ocular immune privilege" Ann N Y Acad Sci 917:297-306

Tang et al. (2004) "In vitro-expanded antigen-specific regulatory T cells suppress autoimmune diabetes" J Exp Med 199:1455-1465

Taylor (1999) "Ocular immunosuppressive microenvironment" 73:72-89 [0131]

Taylor (2003) "Modulation of regulatory T cell immunity by the neuropeptide alpha-melanocyte stimulating hormone" Cell Mol Biol (Noisy-le-grand) 49:143-149

Taylor (2005) "The immunomodulating neuropeptide alpha-melanocyte-stimulating hormone (alpha-MSH) suppresses LPS-stimulated TLR4 with IRAK-M in macrophages" J Neuroimmunol 162:43-50

Taylor et al. (1992) "Identification of alpha-melanocyte stimulating hormone as a potential immunosuppressive factor in aqueous humor" Curr Eye Res 11:1199-1206

Taylor et al. (1994a) "Immunoreactive vasoactive intestinal peptide contributes to the immunosuppressive activity of normal aqueous humor" J Immunol 153:108071086

Taylor et al. (1994b) "Alpha-melanocyte-stimulating hormone suppresses antigen-stimulated T cell production of gamma-interferon" Neuroinununomodulation 1:188-194

Taylor et al. (1996) "Inhibition of antigen-stimulated effector T cells by human cerebrospinal fluid" Nenroimmimomodulation 3:112-118 [0137]

Taylor et al. (2003) "Somatostatin is an immunosuppressive factor in aqueous humor" Invest Ophthalmol Vis Sci 44:2644-2629

Teiger et al. (1996) J Clin Invest 97:2891-97

Willheint-et al. "Regulatory effects of 1 alpha,25-dihydroxy vitamin D3 on the cytokine production of human peripheral blood lymphocytes" J Clin Endocrinol Metab 84:3739-3744

Yamagiwa (2001) "A role for TGF-beta in the generation and expansion of CD4+CD25+ regulatory T cells from human peripheral blood" J Immunol 166:7282-7289

Zeller et al. (1999) "Induction of CD4+ T cell alloantigen-specific hyporesponsiveness by IL-10 and TGF-beta" J Immunol 163:3684-3691

Zheng et al. (2002) "Generation ex vivo of TGF-beta-producing regulatory T cells from CD4+CD25− precursors" J Immunol 169:4183-4189

Zheng et al. (2004) "CD4+ and CD8+ regulatory T cells generated ex vivo with IL-2 and TGF-beta suppress a stimulatory graft-versus-host disease with a lupus-like syndrome" J Immunol 172:1531-1539

The invention claimed is:

1. A method of treating ulcerative colitis or ameliorating one or more symptoms thereof, comprising administering to a patient in need thereof an effective amount of a composition comprising a population of T cells with regulatory activity (T regs) obtained by adding IL-10 to autologous CD4+ T cells and to autologous apoptotic peripheral blood mononuclear cells (ACs), incubating the autologous CD4+ T cells and the ACs in the presence of the added IL-10.

2. The method according to claim 1, wherein the apoptotic peripheral blood mononuclear cells were treated with an ECP procedure that employs a photoactivatable compound together with light of a wavelength that activates the photoactivatable compound to induce apoptosis.

3. The method according to claim 2, wherein the photoactivatable compound is a psoralen and the light is UVA.

4. The method according to claim 3, wherein the psoralen is 8-MOP.

5. The method according to claim 1, wherein the IL-10 is present at a concentration of 1 ng/ml to about 100 ng/ml.

6. The method according to claim 1, wherein the IL-10 is present at a concentration of 20 ng/ml.

7. The method according to claim 1 wherein the incubation is for 1 to 14 days.

8. The method according to claim 7 wherein the incubation is for 8 days.

* * * * *